(12) United States Patent
Lee et al.

(10) Patent No.: US 12,037,575 B2
(45) Date of Patent: Jul. 16, 2024

(54) METHOD AND APPARATUS OF ISOLATING STROMAL CELLS FROM BIOLOGICAL TISSUE WITHOUT USING ENZYME

(71) Applicant: Hee Young Lee, Seoul (KR)

(72) Inventors: Hee Young Lee, Seoul (KR); Hyun Jin Yang, Seoul (KR)

(*) Notice: Subject to any disclaimer, the term of this patent is extended or adjusted under 35 U.S.C. 154(b) by 191 days.

(21) Appl. No.: 16/636,830

(22) PCT Filed: Aug. 23, 2017

(86) PCT No.: PCT/KR2017/009199
§ 371 (c)(1),
(2) Date: Feb. 5, 2020

(87) PCT Pub. No.: WO2019/031641
PCT Pub. Date: Feb. 14, 2019

(65) Prior Publication Data
US 2020/0370002 A1    Nov. 26, 2020

(30) Foreign Application Priority Data
Aug. 7, 2017   (KR) .......................... 10-2017-0099447

(51) Int. Cl.
*C12M 1/00*    (2006.01)
*C12M 1/12*    (2006.01)
(Continued)

(52) U.S. Cl.
CPC ............ *C12M 47/04* (2013.01); *C12M 25/02* (2013.01); *C12M 35/08* (2013.01); *C12N 5/0081* (2013.01); *C12N 2509/10* (2013.01)

(58) Field of Classification Search
None
See application file for complete search history.

(56) References Cited

U.S. PATENT DOCUMENTS

| 4,994,388 A * | 2/1991 | Hillegas ................ C12M 23/20 435/402 |
| 2005/0054101 A1 * | 3/2005 | Felder .................... C12M 25/16 435/383 |

(Continued)

FOREIGN PATENT DOCUMENTS

| KR | 10-0842378 B1 | 7/2008 |
| KR | 10-2013-0073717 A | 7/2013 |

(Continued)

OTHER PUBLICATIONS

Christine Poon. "Measuring the density and viscosity of culture media for optimized computational fluid dynamics analysis of in vitro devices". Journal of the Mechanical Behavior of Biomedical Materials. 126. 2021. (Year: 2021).*

(Continued)

*Primary Examiner* — Holly Kipouros
*Assistant Examiner* — Nathan G Esperon
(74) *Attorney, Agent, or Firm* — Sughrue Mion, PLLC (57) ABSTRACT

Provided are a method and an apparatus for isolating stromal cells from biological tissue without using an enzyme, in which spontaneous migration of the stromal cells of the biological tissue is induced to move the stromal cells to the outside of the biological tissue, wherein the induction of the spontaneous migration of the stromal cells is performed in a state in which the biological tissue is attached to an attachment member formed of a material to which biological tissue is attachable, and is performed in a culture medium in which the stromal cells can survive.

12 Claims, 6 Drawing Sheets

(51) Int. Cl.
*C12M 1/42* (2006.01)
*C12N 5/00* (2006.01)

(56) References Cited

U.S. PATENT DOCUMENTS

| | | | |
|---|---|---|---|
| 2005/0084961 A1* | 4/2005 | Hedrick | A61K 35/28 435/293.1 |
| 2014/0113372 A1* | 4/2014 | Haque | C12N 5/0623 435/402 |
| 2014/0234829 A1* | 8/2014 | Ladtkow | C12N 5/0641 435/283.1 |
| 2016/0083690 A1* | 3/2016 | Birch | A61L 27/18 424/490 |
| 2017/0166853 A1 | 6/2017 | Ekeroth | |
| 2017/0292110 A1* | 10/2017 | Simpson | B01D 21/0012 |

FOREIGN PATENT DOCUMENTS

| | | | |
|---|---|---|---|
| KR | 20130073717 | * | 7/2013 |
| KR | 10-2016-0119503 A | | 10/2016 |
| KR | 10-2017-0073367 A | | 6/2017 |

OTHER PUBLICATIONS

"Bisphenol A polycarbonate". Chemical Entry Polymers: A Property Database 2020. Accessed: Mar. 11, 2022. (Year: 2022).*
"Polypropylene". Chemical Entry Polymers: A Property Database 2020. Accessed: Mar. 11, 2022. (Year: 2022).*
The Engineering Toolbox. "Water—Density, Specific Weight and Thermal Expansion Coefficients". Accessed: Nov. 22, 2023. URL: https://www.engineeringtoolbox.com/water-density-specific-weight-d_595.html (Year: 2023).*
Serini. "Polycarbonates". Ullmann's Encyclopedia of Industrial Chemistry. 2012. (Year: 2012).*
Cherry, et al. "Physical Mechanisms of Cell Damage in Microcarrier Cell Culture Bioreactors". Biotechnology and Bioengineering, vol. 32, pp. 1001-1014 (1988) (Year: 1988).*
International Search Report for PCT/KR2017/009199 dated May 4, 2018 (PCT/ISA/210).

* cited by examiner

METHOD AND APPARATUS OF ISOLATING STROMAL CELLS FROM BIOLOGICAL TISSUE WITHOUT USING ENZYME

CROSS REFERENCE TO RELATED APPLICATIONS

This application is a National Stage of International Application No. PCT/KR2017/009199 filed Aug. 23, 2017, claiming priority based on Korean Patent Application No. 10-2017-0099447 filed Aug. 7, 2017.

TECHNICAL FIELD

The present disclosure relates to a method and apparatus for isolating stromal cells from biological tissue, and more particularly, to a method and apparatus for isolating stromal cells from biological tissue without using an enzyme.

BACKGROUND ART

Methods of isolating stromal cells from biological tissue of an animal may be classified into a method of isolating stromal cells from biological tissue of an animal using an enzyme and a method of isolating stromal cells from biological tissue of an animal without using an enzyme.

The method of isolating stromal cells from biological tissue of an animal using an enzyme may include a method of using an enzyme at an initial isolation stage or a method of using an enzyme at a harvest or subculture stage.

At the initial isolation stage of isolating stromal cells from biological tissue, collagen tissues strongly attached to the stromal cells in the biological tissue while covering the stromal cells are dissolved using an enzyme such as collagenase to dissolve the stromal cells in the biological tissues, and the stromal cells are obtained by cleaning the enzyme in the dissolved stromal cells. In this case, however, there are problems such as toxicity, costs and a treatment time of the enzyme and a risk of heterologous viruses.

When isolated stromal cells are grown in an incubator at the initial isolation stage of isolating the stromal cells from the biological tissue, cell confluency may increase and thus an enzyme such as trypsin may be used for subculture. However, the enzyme used in this case is a component extracted from the gastric juice of a heterologous animal and thus stability is low.

In the method of isolating stromal cells from biological tissue of an animal without using an enzyme, at an initial isolation stage, the biological tissue is finely cut using ultrasonic waves, laser or strong sound pressure to destroy collagen and the stromal cells are isolated through centrifugation. However, in this case, a probability that stromal cells are completely isolated from the collagen is extremely low and considerable damages may be caused to the stromal cells. Thus, the yield of this method is less than 5% and a process thereof is complicated, compared to the method of isolating stromal cells using an enzyme.

In the method of isolating stromal cells from biological tissue of an animal without using an enzyme, at a harvest or subculture stage, cells are grown on surfaces of microbeads with different specific gravity to culture and proliferate isolated stromal cells, the microbeads on which the cells are grown are mixed with a liquid to cause a collision between the microbeads, and escaping cells are collected, or stromal cells are cultured and proliferated on a plane and scraped with a scraper. However, in this case, because the microbeads are spherical, an effect of escape of the cells proliferated on the microbeads during the collision between the cells cannot be maximized, and the number of escaping cells scraped with the scraper is not large and the cells may be damaged during the scraping of the cells.

When biological tissue such as adipose tissue is cultured, the adipose tissue is put into a container in which a culture medium is fully filled to induce the cultured adipose tissue to float on the culture medium and be attached to upper inner side surfaces of the container, based on a fact that the adipose tissue floats on the culture medium. However, in this case, the side surfaces to which the cultured adipose tissue is attached are planar, and thus, an area of the side surfaces to which the cultured adipose tissue is attached and culture efficiency cannot be maximized.

DETAILED DESCRIPTION OF THE INVENTION

Technical Problem

The present disclosure is mainly directed to providing a method and apparatus for moving stromal cells surrounded by collagen in biological tissue to the outside of the biological tissue by spontaneous migration without using an enzyme by finely cutting the biological tissue and input the stromal cells into a culture medium, and thus, problems, such as toxicity, costs and a treatment time of the enzyme, a risk of heterologous virus, and instability caused by use of an enzyme having a component extracted from the gastric juice of a heterologous animal, may be prevented and stromal cells that are in a relatively intact natural condition may be isolated from biological tissue without using an enzyme, thereby increasing isolation efficiency.

The present disclosure is also directed to providing a method and apparatus for effectively scraping, from biological tissue, stromal cells moving out of the biological tissue by spontaneous migration, and thus, problems, such as toxicity, costs and a treatment time of an enzyme, a risk of heterologous virus, and instability caused by use of an enzyme having a component extracted from the gastric juice of a heterologous animal, may be prevented and an efficiency of isolating stromal cells from biological tissue may be increased.

Technical Solution

To address the above-described problems, one aspect of the present disclosure provides a method of isolating stromal cells from biological tissue without using an enzyme, the method including inducing spontaneous migration of the stromal cells of the biological tissue to move the stromal cells to the outside of the biological tissue, wherein the induction of the spontaneous migration of the stromal cells is performed in a state in which the biological tissue is attached to an attachment member formed of a material to which the biological tissue is attachable, and performed in a culture medium in which the stromal cells are survivable.

In one embodiment, the method may further include finely cutting the biological tissue such that at least a portion of the stromal cells is exposed to the outside between collagens surrounding the stromal cells in the biological tissue.

In one embodiment, the method may further include isolating the stromal cells moving to the outside of the attachment member from the biological tissue, and the isolation of the stromal cells may be performed by applying a physical force to the stromal cells attached to the attachment member.

In one embodiment, the physical force applied to the stromal cells moving to the outside of the biological tissue may be a force generated by causing the stromal cells moving to the outside of the biological tissue to make a turbulent motion, together with the culture medium.

In one embodiment, the method may further include collecting the stromal cells isolated from the biological tissue.

Another aspect of the present disclosure provides a method of isolating stromal cells from biological tissue without using an enzyme, the method including (1) finely cutting the biological tissue; (2) attaching the finely cut biological tissue, in a culture medium, to an attachment member formed of a material to which the biological tissue is attachable; (3) moving the stromal cells out of the biological tissue by inducing spontaneous migration of the stromal cells on the attachment member; and (4) isolating the stromal cells moving out of the biological tissue from the attachment.

In one embodiment, the finely cutting of the biological tissue in operation (1) may include finely cutting the biological tissue to expose at least a portion of the stromal cells to the outside between collagens surrounding the stromal cells in the biological tissue.

In one embodiment, the isolating of the stromal cells in operation (4) may be performed by applying a physical force to the stromal cells to cause a collision between a plurality of attachment members through a turbulent motion of the culture medium, wherein the stromal cells moving to the outside of the biological tissue are arranged in the plurality of attachment members.

In one embodiment, the method may further include (5) collecting the stromal cells isolated from the biological tissue.

In one embodiment, operations (2) to (4) may be sequentially repeated.

In one embodiment, operations (2) to (4) may be sequentially repeated after replacing at least one selected from the group consisting of the biological tissue, the culture medium, and the attachment member.

In the above embodiments, the biological tissue may include at least one selected from the group consisting of skin, fat, cartilage, mucous membrane, blood vessel, ligament, heart, brain, placenta, umbilical cord, amniotic membrane, muscle, and peripheral nerve.

In the above embodiments, the culture medium may include at least one selected from the group consisting of Dulbecco's Modified Eagle's Medium (DMEM) and fetal bovine serum.

Another aspect of the present disclosure provides an apparatus for isolating stromal cells from biological tissue without using an enzyme, the apparatus including an attachment member configured to move the stromal cells to the outside of the biological tissue by inducing spontaneous migration of the stromal cells of the biological tissue by attaching the biological tissue to the attachment member in a culture medium, wherein the attachment member has a lower or higher average specific gravity than that of the culture medium.

In one embodiment, when the attachment member has the lower average specific gravity than that of the culture medium, the attachment member comprises at least one selected from the group consisting of polypropylene, polyethylene, polyurethane, extracellular matrix (ECM), collagen, polydioxanone, polycaprolactone, poly(L-lactide) (PLLA), poly(lactic-co-glycolic acid) (PLGA), poly(lactic acid) (PLA), pterolyglutamic acid (PGA), hyaluronic acid, and silicone.

In one embodiment, when the attachment member has the higher average specific gravity than that of the culture medium, the attachment member comprises at least one selected from the group consisting of Teflon, polycarbonate, polyethylene, phthalate, polystyrene, polyurethane, extracellular matrix (ECM), collagen, polydioxanone, polycaprolactone, poly(L-lactide) (PLLA), poly(lactic-co-glycolic acid) (PLGA), pol(lactic acid) (PLA), pterolyglutamic acid (PGA), hyaluronic acid, and silicone.

In one embodiment, the biological tissue finely cut to expose at least a portion of the stromal cells to the outside between collagens surrounding the stromal cells in the biological tissue may be attached to the attachment member.

In one embodiment, the attachment member may be further configured to not only induce spontaneous migration of the stromal cells of the biological tissue to move the stromal cells to the outside of the biological tissue, when the biological tissue is attached to the attachment member in the culture medium, but also isolate the stromal cells moving to the outside of the biological tissue from the biological tissue.

In one embodiment, the attachment member may include a main body forming an area in which the stromal cells moving to the outside of the biological tissue by spontaneous migration are arranged, and a scraping portion extending outward from the main body, having a thickness less than that of the main body, and having a shape for scraping stromal cells arranged on another attachment member.

In one embodiment, an angle formed by corners of a cross section of the scraping portion may be an acute angle.

In one embodiment, the apparatus may further include a container for accommodating a culture medium, biological tissue and an attachment member therein.

In one embodiment, the container may include an inclined portion forming an accommodation space for accommodation of the culture medium, the biological tissue, and the attachment member, the inclined portion being formed to cause centrifugation when the container rotates.

In one embodiment, the container may be further configured to induce turbulence of the culture medium by normal operation and reverse rotation.

In one embodiment, the container may further include a barrier membrane configured to block the biological tissue and allow the culture medium to pass therethrough, the barrier membrane being arranged at a position where the barrier membrane is immersed into the culture medium to prevent the biological tissue from floating on the culture medium, when the container is stopped.

In one embodiment, the container may include a convergence part provided at a position to which a maximum centrifugal force is applied and configured to converge the stromal cells isolated from the biological tissue by a centrifugal force.

In one embodiment, the container may further include a filter provided in a path from the accommodation space to the convergence part and configured to allow movement of the stromal cells by a centrifugal force and block movement of the biological tissue and the attachment member.

In one embodiment, the container may further include a stromal cell discharge part on the convergence parts to discharge the stromal cells converged on the convergence part to the outside.

In one embodiment, the container may further include a culture medium through-tube configured to inject or discharge the culture medium, the culture medium throughtube extending from the outside to the accommodation space.

In one embodiment, the container may further include a gas inlet through which a gas is injected for internal disinfection.

Advantageous Effects

It is a main effect of the present disclosure to provide a method and apparatus for moving stromal cells surrounded by collagen in biological tissue to the outside of the biological tissue by spontaneous migration without using an enzyme by finely cutting the biological tissue and input the biological tissue into a culture medium, and thus, problems, such as toxicity, costs and a treatment time of the enzyme, a risk of heterologous virus, and instability caused by use of an enzyme having a component extracted from the gastric juice of a heterologous animal, may be prevented and stromal cells that are in a relatively intact natural condition may be isolated from biological tissue without using an enzyme, thereby increasing isolation efficiency.

It is another main effect of the present disclosure to provide a method and apparatus for effectively scraping, from biological tissue, stromal cells moving to the outside of the biological tissue by spontaneous migration, and thus, problems, such as toxicity, costs and a treatment time of the enzyme, a risk of heterologous virus, and instability caused by use of an enzyme having a component extracted from the gastric juice of a heterologous animal, may be prevented and an efficiency of isolating stromal cells from biological tissue may be increased.

MODE OF THE DISCLOSURE

Details of matters for carrying out the present disclosure will be described hereinafter. The following description is provided as examples to help those of ordinary skill in the art understand matters for carrying out the present disclosure and thus various modifications may be made therein and the scope of the present disclosure is not limited by the following description.

1. Method of Isolating Stromal Cells from Biological Tissue without Using an Enzyme This method is a method of isolating stromal cells from biological tissue without using an enzyme, in which spontaneous migration of the stromal cells of the biological tissue is induced to move the stromal cells to the outside of the biological tissue.

The biological tissue may include at least one selected from the group consisting of skin, fat, cartilage, mucous membrane, blood vessel, ligament, heart, brain, placenta, umbilical cord, amniotic membrane, muscle, and peripheral nerve.

Figure 1:
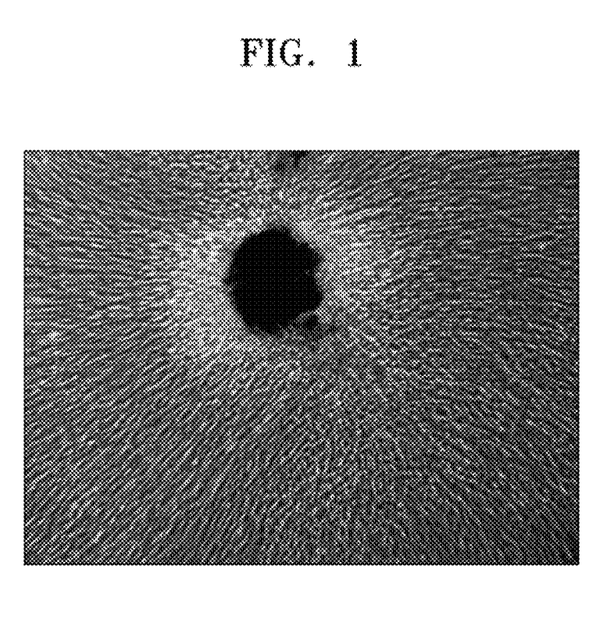
FIG. 1 is a photograph of an image of stromal cells moving out of biological tissue.

The spontaneous migration of the stromal cells of the biological tissues refers to spontaneous movement of the stromal cells to the outside while penetrating collagen surrounding the stromal cells in the biological tissue. An example of an image of stromal cells continuously moving out of biological tissue by spontaneous migration is illustrated in FIG. 1.

The movement of the stromal cells out of the biological tissues by spontaneous migration may be a very important characteristic for isolation of the stromal cells from the biological tissue without using an enzyme. The present disclosure provides a method of isolating stromal cells from biological tissue without using an enzyme by inducing spontaneous migration of the stromal cells of the biological tissue to move the stromal cells to the outside.

Figure 2:
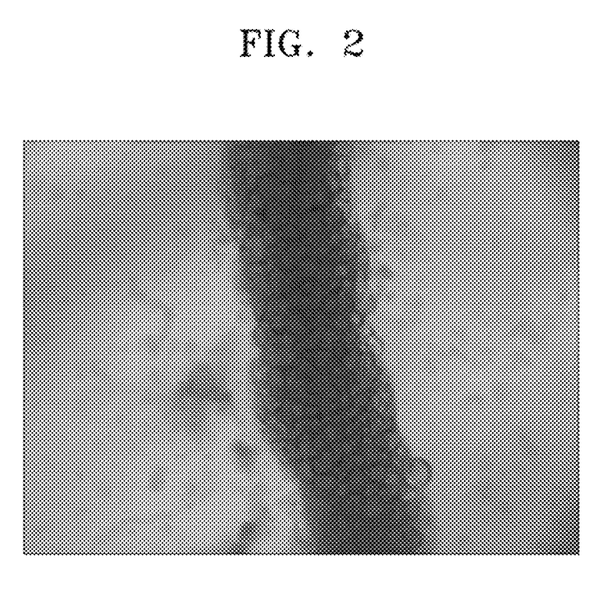
FIG. 2 is a photograph of an image of adipocytes attached to a chromic catgut.

The spontaneous migration of the stromal cells may be more effectively carried out in a state in which the biological tissue is attached to a member formed of a material to which biological tissue is attachable. For example, as illustrated in FIG. 2, when adipose tissue is attached to a chromic catgut, adipocytes may move and be attached to the outside of the adipose tissue by spontaneous migration of the adipocytes. As described above, the spontaneous migration of the stromal cells may be more effectively induced in a state in which the biological tissue is attached to a member formed of a material to which biological tissue is attachable, thereby more effectively isolating the stromal cells from the biological tissue. Here, various members may be employed as the member formed of the material to which the biological tissue is attachable. For example, a member formed of the same material as a chromic catgut may be used.

The spontaneous migration of the stromal cells is preferably induced in a culture medium in which stromal cells can survive. Therefore, the stromal cells moving out of the biological tissue may be isolated together with the culture medium so that the stromal cells may be collected and cultured without being damaged.

The culture medium may include at least one selected from the group consisting of Dulbecco's Modified Eagle's Medium (DMEM) and fetal bovine serum.

A culture medium having the same average specific gravity as the biological tissue may be used for a distribution of the biological tissue in the entire culture medium so that the stromal cells moving out of the biological tissue by spontaneous migration may be efficiently isolated together with the culture medium.

When the spontaneous migration of the stromal cells is carried out in a state in which the biological tissue is attached in the culture medium to an attachment member formed of a material to which the biological tissue is attachable, a culture medium having the same average specific gravity as or a higher average specific gravity than those of the attachment member and the biological tissue may be used. This is because the biological tissue is likely to come into contact with the attachment member when the attachment member and the biological tissue are distributed in the entire culture medium or near a surface of the culture medium. Thus, the biological tissue may be more effectively attached to the attachment member and spontaneous migration of stromal cells may be induced more effectively.

The biological tissue is more preferably finely cut and attached to the attachment member such that at least a portion of the stromal cells is exposed to the outside between collagens surrounding the stromal cells. Therefore, spontaneous migration of the stromal cells in the biological tissue may be easily induced to more efficiently isolate the stromal cells from the biological tissue. In this case, the biological tissue may be cut by laser or the like.

After the stromal cells move out of the biological tissue by spontaneous migration, a physical force may be applied to the stromal cells to be isolated from the biological tissue. For example, after the stromal cells move out of the biological tissue in the culture medium by spontaneous migration, the stromal cells may be isolated from the biological tissue by applying a physical force to the stromal cells through a turbulent motion of the stromal cells together with the culture medium. When the stromal cells move out of the biological tissue by spontaneous migration on the attachment member in the culture medium, the stromal cells may be efficiently isolated from the biological tissue by applying a physical force to the stromal cells on the attachment member through a turbulent motion of the stromal cells together with the culture medium or by applying a stronger physical force to the stromal cells on the attachment member by causing a collision between a plurality of attachment members through turbulent motions of the plurality of attachment members together with the culture medium.

The stromal cells are collected externally after being isolated from the biological tissue. The collected stromal cells may be grown in the culture medium by culture or subculture. When the stromal cells are isolated from the biological tissue in the culture medium, the stromal cells may be collected together with the culture medium and thus be isolated and cultured or subcultured more efficiently.

2. Apparatus for Isolating Stromal Cells from Biological Tissue without Using an Enzyme The apparatus is an apparatus for isolating stromal cells from biological tissue without using an enzyme, and includes an attachment member to which biological tissue is attached in a culture medium to induce spontaneous migration of stromal cells of the biological tissue so as to move the stromal cells out of the biological tissue.

The attachment member may be formed of various materials, provided that spontaneous migration of stromal cells of biological tissue be induced to move the stromal cells out of the biological tissue by attaching the biological tissue to the attachment member in the culture medium. For example, the attachment member may be formed of a material that is the same as or similar to that of the biological tissue to stably or efficiently attach the biological tissue thereto. When the attachment member is arranged in the culture medium while the biological tissue is attached to at least a portion of a surface of the attachment member, the biological tissue distributed in the culture medium may be more easily attached to the surface of the attachment member to which the same biological tissue is attached.

Figure 3:
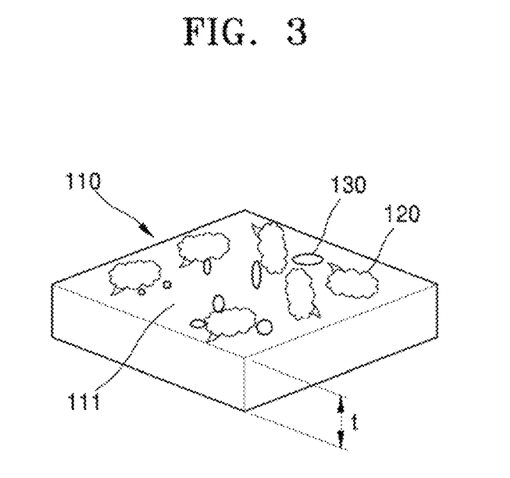
FIG. 3 is a schematic view of movement of stromal cells of biological tissue on an attachment member to the outside of the biological tissue by spontaneous migration.

The attachment member may be in various forms, provided that spontaneous migration of stromal cells of biological tissue be induced to move the stromal cells out of the biological tissue by attaching the biological tissue is attached to the attachment member in the culture medium. For example, as illustrated in FIG. 3, an attachment member 110 may include a main body 111 having a surface which is a region to which a plurality of finely cut biological tissues 120 are attached and on which stromal cells 130 of the plurality of biological tissues 120 moving out of the biological tissues 120 by spontaneous migration are arranged. To this end, the attachment member 110 may be formed in an overall flat cubic shape. For example, the attachment member 110 of FIG. 3 may be formed in a tetragonal prismatic shape but is not limited thereto and may be formed in various shapes such as a cylindrical shape, a triangular prismatic shape and a pentagonal prismatic shape.

A thickness t of the attachment member 110 is preferably large enough for the attachment member 110 to have rigidity to withstand the plurality of finely cut biological tissues 120 attached thereto and a turbulent motion of a culture medium, and at the same time is preferably small enough for the attachment member 110 to be smoothly moved by the turbulent motion of the culture medium.

When a concavo-convex structure is formed on at least a portion of a surface of the attachment member, an area of the biological tissue in contact with the attachment member may increase and thus the biological tissue may be more easily attached to the attachment member.

The attachment member may have various specific gravities, provided that the biological tissue be attached to the attachment member in the culture medium and spontaneous migration of the stromal cells of the biological tissue be induced to move the stromal cells out of the biological tissue.

When the biological tissue has a lower average specific gravity than that of the culture medium and thus a most part thereof is distributed near the surface of the culture medium, it is preferable that the attachment member have a lower average specific gravity than that of the culture medium. This is because a most part of the attachment member is distributed near the surface of the culture medium, similar to the biological tissue, the attachment member is more likely to come into contact with the biological tissue, thereby greatly increasing a possibility that the biological tissue will be attached to the attachment member. Therefore, in this case, the stromal cells of the biological tissue are more likely to move out of the biological tissue by spontaneous migration on the attachment member.

When the attachment member has a lower average specific gravity than that of the culture medium, the attachment member may include at least one selected from the group consisting of polypropylene, polyethylene, polyurethane, extracellular matrix (ECM), collagen, polydioxanone, polycaprolactone, poly(L-lactide) (PLLA), poly(lactic-co-glycolic acid) (PLGA), poly(lactic acid) (PLA), pterolyglutamic acid (PGA), hyaluronic acid, and silicone.

When the biological tissue has a higher average specific gravity than that of the culture medium and thus a most part thereof is distributed near a lower surface of the culture medium, it is preferable that the attachment member have a higher average specific gravity than that of the culture medium. This is because a most part of the attachment member is distributed near the low surface of the culture medium, similar to the biological tissue, the attachment member is more likely to come into contact with the biological tissue, thereby greatly increasing a possibility that the biological tissue will be attached to the attachment member. Therefore, in this case, the stromal cells of the biological tissue are more likely to move out of the biological tissue by spontaneous migration on the attachment member.

When the attachment member has a higher average specific gravity than that of the culture medium, the attachment member may include at least one selected from the group consisting of Teflon, polycarbonate, polyethylene, phthalate, polystyrene, polyurethane, extracellular matrix (ECM), collagen, polydioxanone, polycaprolactone, poly(L-lactide) (PLLA), poly(lactic-co-glycolic acid) (PLGA), pol(lactic acid) (PLA), pterolyglutamic acid (PGA), hyaluronic acid, and silicone.

When the biological tissue has the same average specific gravity as the culture medium and thus is dispersed and distributed in the entire culture medium, it is preferable that the attachment member have the same average specific gravity as the culture medium. This is because the attachment member is dispersed and distributed in the entire culture medium, similar to the biological tissue, the attachment member is more likely to come into contact with the biological tissue, thereby greatly increasing a possibility that the biological tissue will be attached to the attachment member. Therefore, in this case, the stromal cells of the biological tissue are more likely to move out of the biological tissue by spontaneous migration on the attachment member.

The biological tissue attached to the attachment member is preferably finely cut such that at least a portion of the stromal cells is exposed to the outside between collagens surrounding the stromal cells of the biological tissue. Therefore, spontaneous migration of stromal cells is more likely to be induced, thereby promoting isolation of the stromal cells from the biological tissue.

The attachment member may not only induce spontaneous migration of the stromal cells of the biological tissue to move the stromal cells out of the biological tissue, when the biological tissue is attached to the attachment member in the culture medium but also isolate the stromal cells moving out of the biological tissue by spontaneous migration from the biological tissue. Therefore, the attachment member may promote not only the movement of the stromal cells out of the biological tissue by spontaneous migration but also the isolation of the stromal cells moving out of the biological tissue from the biological tissue.

The stromal cells moving out of the biological tissue by spontaneous migration may be isolated from the biological tissue in various ways.

Figure 4:
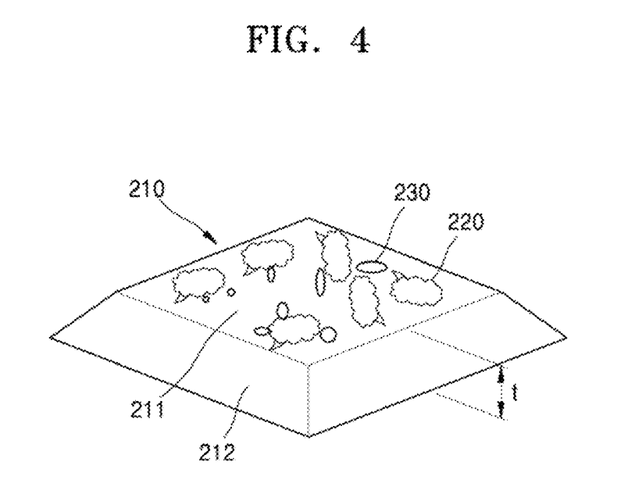
FIG. 4 is a schematic view of movement of stromal cells of biological tissue on another type of attachment member to the outside of the biological tissue by spontaneous migration.
Figure 5:
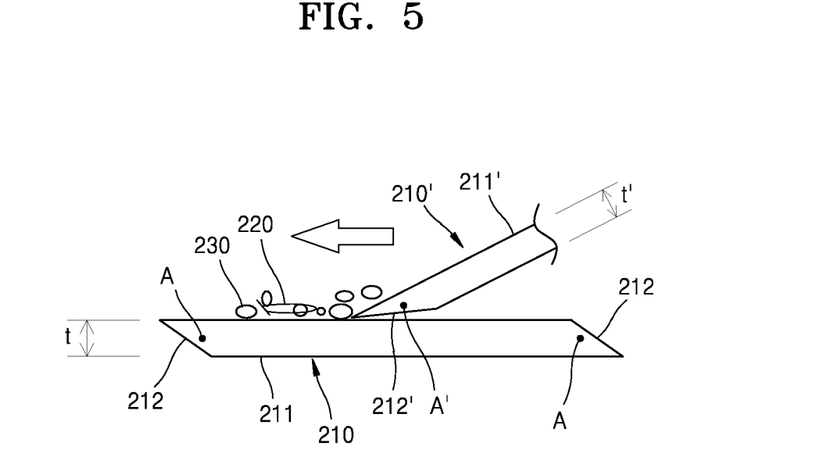
FIG. 5 is a schematic view of scraping of stromal cells, which move to the outside of biological tissue on an attachment member by spontaneous migration, by another attachment member.

For example, the attachment member may be configured to scrape the stromal cells moving out of the biological tissue on the attachment member. Thus, the stromal cells may be isolated from the biological tissue and moved into the culture medium when a physical force is applied to the stromal cells. To this end, as illustrated in FIG. 4, the attachment member 210 may include a main body 211 which is a region to which biological tissue 220 is attached and on which stromal cells 230 moving out of the biological tissue 220 by spontaneous migration are arranged, and may further include a scraping portion 212 extending outward from the main body 211, having a thickness less than a thickness t of the main body 211, and having a shape for scraping stromal cells arranged on a different attachment member. An angle formed by corners of a cross section of the scraping portion 212 may be an acute angle less than 90 degrees. The stromal cells 230 moving out of the biological tissue 220 by spontaneous migration and arranged on an outer side of the biological tissue 220 or on the attachment member 210 may be easily isolated from the biological tissue 220 or the attachment member 210 and moved into the culture medium by the scraping portion 212. For example, as illustrated in FIG. 5, stromal cells 230 moving out of biological tissue 220 on a first attachment member 210 and arranged on an outer surface of the biological tissue 220 or on the first attachment member 210 may be easily scraped by a second scraping portion 212', which extends outward from a second main body 211' and has a thickness less than a thickness t' of the second main body 211', during collision with an adjacent second attachment member 210' making a turbulent motion together with a culture medium, thereby promoting the stromal cells 230 to be isolated from the biological tissue 220 or the first attachment member 210 and moved into the culture medium. The first scraping portion 212 is also configured to scrape stromal cells arranged on another attachment member. An angle A formed by corners of a cross section of the first scraping portion 212 and an angle A' formed by corners of a cross section of the second scraping portion 212' are acute angles less than 90 degrees so that the first scraping portion 212 may have a thickness less than the thickness t of the first man boy 211 and the second scraping portion 212' may have a thickness less than the thickness t' of the second main body 211'. However, a scraping portion is not limited to the shapes illustrated in FIGS. 4 and 5 and may be in various shapes for isolation of stromal cells on an attachment member.

The apparatus may further include a container for accommodating a culture medium, biological tissue and an attachment member therein.

Figure 6:
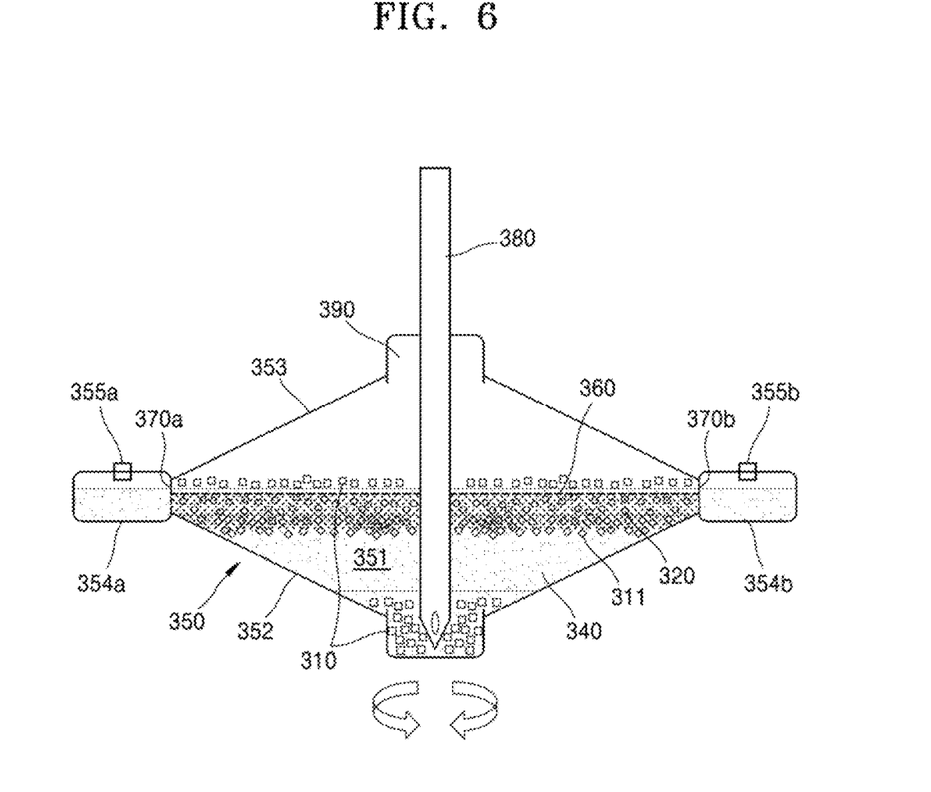
FIG. 6 is a view illustrating a state in which a culture medium, biological tissue and an attachment member are arranged in different layers in a container.

The container includes a space for accommodating the culture medium, the biological tissue and the attachment member. For example, as illustrated in FIG. 6, a container 350 may include an accommodation space 351 in which a culture medium 340, biological tissue 320, and attachment members 310 and 311 may be accommodated. However, the accommodation space 351 is not limited thereto and may have various shapes in which the culture medium 340, the biological tissue 320, and the attachment members 310 and 311 may be accommodated.

The accommodation space 351 includes an inclined portion 352 configured to cause centrifugation by rotation, and a circular cross section, the radius of which increases in an upward direction. An upper portion of the accommodation space 351 is covered with a cover 353. The cover 353 prevents the culture medium 340, the biological tissue 320 and the attachment members 310 and 311 which are accommodated in the accommodation space 351 from leaking to the outside. In addition, the cover 353 blocks leakage of the culture medium 340 to the outside due to a turbulent motion of the culture medium 340 due to forward and reverse rotations of the container 350. It may be advantageous for centrifugation by rotation when the cover 353 include an inclined portion with an inclination angle opposite to that of the inclined portion 352 of the accommodation space 351, and a circular cross section, the radius of which decreases in the upward direction.

The container may repeatedly make a normal rotation in one direction and a reverse rotation in a reverse direction to induce turbulence of the culture medium in the accommodation space. Turbulent motions of the biological tissue and the attachment member are caused by the turbulence of the culture medium. Therefore, the stromal cells may move out of the biological tissue attached to the attachment member by spontaneous migration and thus are isolated from the biological tissue or the attachment member and moved into the culture medium. In addition, as the container rotates in one direction, a centrifugal force may be applied to the stromal cells distributed in the culture medium to isolate the stromal cells from the biological tissue and the attachment member, thereby collecting the stromal cells together with the culture medium.

The container may further include a barrier membrane at a position at which the barrier membrane is immersed in the culture medium in the accommodation space when the container is stopped. The barrier membrane has a lower average specific gravity than that of the culture medium and thus block the biological tissue floating on the culture medium from floating on a surface of the culture medium, so that the biological tissue may be brought into contact with the attachment member to be attached to the attachment member. To this end, the barrier membrane includes a through hole that blocks the barrier membrane but allows the culture medium to pass therethrough. The attachment member cannot pass through the through hole of the barrier membrane.

For example, as illustrated in FIG. 6, a barrier membrane 360 is provided at a position at which it is immersed in the culture medium 340, e.g., near a water surface below the surface of the culture medium 340, in the accommodation space 351 when the container 350 is stopped. The barrier membrane is provided with a plurality of through holes, and the through holes have a size adjusted to allow the culture medium 340 to pass therethrough but block the biological tissue 320 and the attachment members 310 and 311. The biological tissue 320 injected into the culture medium 340 under the barrier membrane 360 is blocked by the barrier membrane 360 when the average specific gravity of the barrier membrane 320 is lower than that of the culture medium 340 and thus does not flow on the surface of the culture medium 340 and is gathered near a lower portion of the barrier membrane 360. The attachment member 311 having a lower average specific gravity than that of the culture medium 340 among the attachment members 310 and 311 injected into the culture medium 340 under the barrier membrane 360 is blocked by the barrier membrane 360 and thus does not float on the surface of the culture medium 340 but is gathered below the lower portion of the barrier membrane 360. When the biological tissue 320 has a lower average specific gravity than that of the attachment member 311, the attachment member 311 is gathered under a layer at which the biological tissue 320 is collected. Accordingly, the biological tissue 320 is located adjacent to or overlaps the attachment member 311 thus forming a layer, thereby greatly increasing a possibility that the attachment member 311 will be brought into contact with the attachment member 311 and attached to the attachment member 311. As a result, a possibility that the stromal cells will move out of the biological tissue 320 attached to the attachment member 311 by spontaneous migration increases greatly.

In addition, the barrier membrane may block movement of the attachment member to an upper portion of the culture medium when the attachment member makes a turbulent motion due to turbulence of the culture medium and thus the stromal cells moving out of the biological tissue on the attachment member may be prevented from moving out of the culture medium.

The container may include convergence parts at positions to which a maximum centrifugal force is applied to converge the stromal cells isolated from the biological tissue by a centrifugal force. Therefore, the stromal cells isolated from the biological tissues may be converged to be easily discharged to the outside.

For example, as illustrated in FIG. 6, convergence parts 354a and 354b include a first convergence part 354a at a position on an upper edge of the accommodation space 351 to which a maximum centrifugal force is applied, and a second convergence part 354b at a position on the upper edge of the accommodation space 351, which is symmetric to the position of the first convergence part 354a and to which the maximum centrifugal force is applied. Each of the first convergence part 354a and the second convergence part 354b includes a space for accommodation of the converged stromal cells together with the culture medium 340. Because the first and second convergence parts 354a and 354b are provided at the positions to which the maximum centrifugal force is applied, the stromal cells isolated from the biological tissue 320 and distributed in the culture medium 340 are induced to be converged together with the culture medium 340 when centrifugation is performed by the rotation of the container 350. The convergence parts are not limited to those illustrated in FIG. 6 and may include one or three or more convergence parts.

The container may further include filters provided in a path from the accommodation space to the convergence parts and configured to allow movement of the stromal cells by a centrifugal force and block movement of the biological tissue and the attachment member. Therefore, the culture medium in which the stromal cells are distributed may be controlled to be converged on the convergence parts but the biological tissue and the attachment member may be controlled to not be converged on the convergence parts.

For example, as illustrated in FIG. 6, a first filter 370a is provided in a path from the accommodation space 351 to the first convergence part 354a, and a second filter 370b is provided in a path from the accommodation space 351 to the second convergence part 354b. The first filter 370a is located at an entrance of the first convergence part 354a and the second filter 370b is located at an entrance of the second convergence part 354b. A plurality of through holes are formed in the first and second filters 370a and 370b. The through holes have a size appropriate to allow the culture medium 340 in which the stromal cells are distributed to pass therethrough and to block the biological tissue 320 and the attachment members 310 and 311. Accordingly, the first and second filters 370a and 370b allow movement of the culture medium 340 in which the stromal cells are distributed and block movement of the biological tissue 320 and the attachment members 310 and 311, so that culture medium 340 in which the stromal cells are distributed may converge on the first and second convergence parts 354a and 354b, except the biological tissue 320 and the attachment members 310 and 311. The filters are not limited to those illustrated in FIG. 6 and may be arranged at various positions in the path from the accommodation space to the convergence parts.

The container may further include stromal cell discharge parts on the convergence parts to discharge the stromal cells converging on the convergence part to the outside. Accordingly, the stromal cells converging on the convergence parts may be easily discharged to the outside.

For example, as illustrated in FIG. 6, stromal cell discharge parts 355a and 355b include a first stromal cell discharge part 355a provided on the first convergence part 354a to discharge the stromal cells converging on the first convergence part 354a to the outside, and a second stromal cell discharge part 355b provided on the second convergence part 354b to discharge the stromal cells converging on the second convergence part 354b to the outside. The first stromal cell discharge part 355a discharges to the outside the culture medium 340 in which the stromal cells converging on the first convergence part 354a are distributed, and the second stromal cell discharge part 355b discharges to the outside the culture medium 340 in which the stromal cells converged on the second convergence part 354b are distributed. The first and second stromal cell discharge parts 355a and 355b may be tubes connected to outlets formed at the first and second convergence parts 354a and 354b. The stromal cell discharge parts are not limited to those illustrated in FIG. 6 and may include various structures formed on the convergence parts to discharge the stromal cells converged on the convergence parts to the outside.

The container may further include a culture medium through-tube extending from the outside to the accommodation space to inject or discharge the culture medium. The culture medium may be easily injected into or discharged from the accommodation space through the culture medium through-tube.

For example, as illustrated in FIG. 6, the culture medium 340 through-tube 380 includes a tube extending to the inside of the accommodation space 351 from the outside while passing through the cover 353. The culture medium 340 through-tube 380 may sequentially pass through the cover 353 and a central portion of the barrier membrane 360 and extend to the vicinity of a central bottom surface of the accommodation space 351. A rubber sealing member 390 is provided at a central portion of the cover 353 through which the culture medium 340 through-tube 380 passes to tightly seal a central portion of the accommodation space 351 through which the culture medium 340 through-tube 380 passes. The culture medium 340 may be easily injected into the accommodation space 351 from the outside or discharged from the accommodation space to the outside via the culture medium 340 through-tube 380 without opening the culture medium 340 and thus the culture medium 340 may be easily injected or replaced whenever necessary. The culture medium 340 through-tube is not limited to that illustrated in FIG. 6 and may be formed in various configurations which extend from the outside to the accommodation space and through which the culture medium 340 may be injected or discharged.

The container may further include a gas inlet through which a gas is injected for internal disinfection. Therefore, the inside of the container may be easily disinfected.

3. Example

One embodiment of the present disclosure is directed to a method of isolating stromal cells from biological tissue without using an enzyme, the method including (1) finely cutting the biological tissue; (2) attaching the finely cut biological tissue, in a culture medium, to an attachment member formed of a material to which the biological tissue is attachable; (3) inducing spontaneous migration of the stromal cells on the attachment member moving the stromal cells out of the biological tissue; (4) isolating the stromal cells moving out of the biological tissue from the biological tissue; and (5) collecting the stromal cells isolated from the biological tissue.

(1) The finely cutting of the biological tissue includes finely cutting the biological tissue to expose at least a portion of the stromal cells to the outside between collagens surrounding the stromal cells in the biological tissue. The biological tissue may be cut by laser or the like. The spontaneous migration of the stromal cells of the biological tissue may be effectively induced by finely cutting the biological tissue to expose at least a portion of the stromal cells to the outside between collagens surrounding the stromal cells.

(2) The attaching of the finely cut biological tissue in a culture medium to the attachment member formed of the material to which the biological tissue is attachable is performed in a container in which the biological tissue, the culture medium and the attachment member are placed as shown in FIG. 6.

First, the container 350 with the accommodation space 351 for accommodating the biological tissue 320, the culture medium 340 and the attachment members 310 and 311 is prepared. The cover 353 of the container 350 and the barrier membrane 360 are separated from the container 350 and thereafter the finely cut biological tissue 320 prepared in advance and the attachment members 310 and 311 formed of the material to which the biological tissue 320 is attachable are placed in the accommodation space 351. Next, the cover 353 and the barrier membrane 360 are combined with the container 350 and thereafter the culture medium 340 in which stromal cells can survive is injected via the culture medium through-tube 380 extending to the accommodation space 351 while passing through the cover 353 and a central portion of the barrier membrane 360. In this case, the culture medium 340 is injected such that a surface of the culture solution 340 is at a higher level than the blocking membrane 360.

When the culture medium 340 is injected while the biological tissue 320 and the attachment members 310 and 311 are positioned in the accommodation space 351 of the container 350 as described above, the biological tissue 320 and the attachment member 311 which have a lower average specific gravity than that of the culture medium 340 move to the surface of the culture medium 340 and thus are arranged in layers on a lower side of the barrier membrane 360 and the vicinity thereof. In this case, the biological tissue 320 having a lower average specific gravity than that of the attachment member 311 is located in a layer above the attachment member 311 and the attachment member 311 is located in a layer below the biological tissue 320. In this case, the layer in which the biological tissue 320 partially overlaps or is located adjacent to the layer in which the attachment member 311 is arranged and thus an area of the biological tissue 320 in contact with the attachment member 311 greatly increases. The attachment member 310 having a higher average specific gravity than that of the culture medium 340 is arranged at a lower side of the accommodation space 351 below the culture medium 340 and the vicinity thereof. A portion of the attachment member 310 having the higher average specific gravity than that of the culture solution 340 may be arranged on an upper side of the barrier membrane 360. As time passes in a state in which the culture medium 340, the biological tissue 320, and the attachment member 311 are arranged, the biological tissue 320 is attached to the attachment member 311.

(3) The inducing of the spontaneous migration of the stromal cells on the attachment member to move the stromal cells out of the biological tissue includes moving the stromal cells out of the biological tissue 320 by spontaneous migration of the stromal cells in the biological tissue 320 on the attachment member 311 to which the biological tissue 320 is attached, as illustrated in FIG. 6.

The stromal cells in the biological tissue 320 move to an outer side of the biological tissue 320, a surface of the attachment member 311 or into the culture medium 340 by spontaneous migration. In the movement of the stromal cells, stromal cells exposed to the outside between collagens of the biological tissue 320 attached on the attachment member 311 move actively.

(4) The isolating of the stromal cells moving out of the biological tissue from the biological tissue includes isolating from the biological tissue the stromal cells moving out of the biological tissue 320 by spontaneous migration on the attachment member 311 to which the biological tissue 320 is attached and moving the isolate stromal cells into the culture medium 340, as illustrated in FIG. 6.

The isolating of the stromal cells moving out of the biological tissue 320 from the biological tissue 320 and the moving of the isolated stromal cells into the culture medium 340 are performed by alternately repeating a normal rotation and a reverse rotation of the container 350 to apply a physical force to the stromal cells moving out of the biological tissue 320 so as to isolate the stromal cells from the biological tissue 320, as illustrated in FIG. 6. When the normal rotation and the reverse rotation of the container 350 are alternately repeated, turbulence is generated in the culture medium 340, thus causing a turbulent motion of the attachment member 311 immerged in the culture medium solution 340, and therefore, a physical force is applied to the stromal cells moving out of the biological tissue 320 on the attachment member 311, thereby isolating the stromal cells from the biological tissue 320.

Alternatively, when a plurality of attachment members 311 collide with each other due to turbulent motions thereof, stromal cells moving out of the biological tissue 320 on another attachment member 311 may be scraped by the scraping portion (see FIG. 5) on the attachment member 311, thereby promoting isolation of the stromal cells from the biological tissue 320 into the culture medium 340.

Furthermore, as the plurality of attachment members 311 are brought into contact or collision with an inner side of the inclined portion 352 of the container 350, the attachment member 310 having a higher average specific gravity than that of the culture medium 340 and making a turbulent motion, an outer side of the culture medium through-tube 380 or a lower side of the barrier membrane 360 due to turbulent motions of the plurality of attachment members 311, the stromal cells moving out of the biological tissue 320 on the attachment member 311 is promoted to be isolated from the biological tissue 320 and moved into the culture medium 340.

Figure 7:
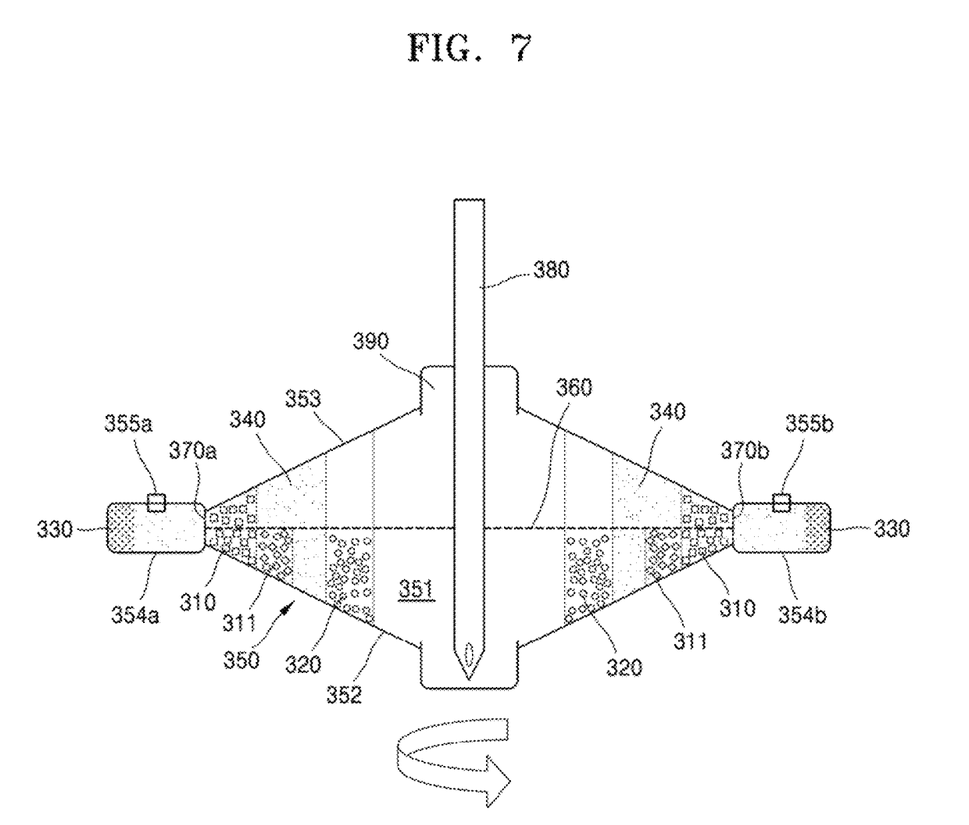
FIG. 7 is a view illustrating a state in which a culture medium, biological tissue and an attachment member in the container are centrifuged.
Figure 8:
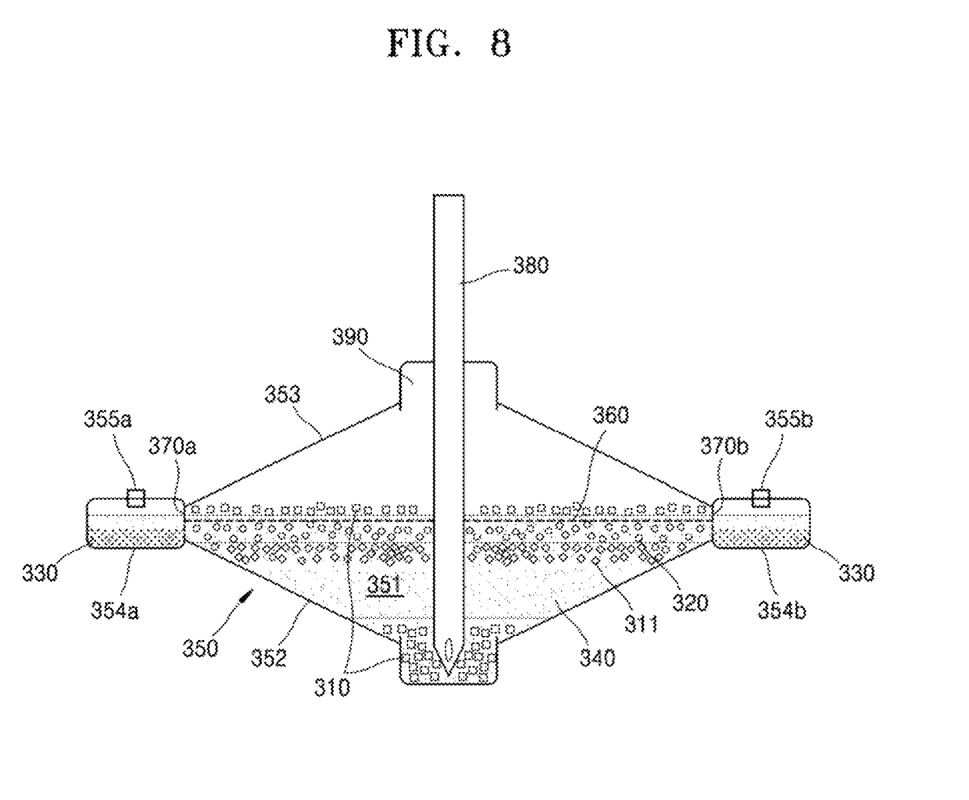
FIG. 8 is a view illustrating a state in which stromal cells isolated from biological tissue in a container converge on convergence parts, together with a culture medium.

(5) The collecting of the stromal cells isolated from the biological tissue is performed by collecting the stromal cells isolated from the biological tissue and moved into the culture medium by isolating the stromal cells from the biological tissue and the attachment member, and includes (a) converging the stromal cells 330, which are isolated from the biological tissue 320 into the culture medium 340, on the convergence parts 354a and 354b by centrifugation, and (b) discharging the stromal cells 330 converging on the convergence parts 354a and 354b to the outside, as illustrated in FIGS. 7 and 8.

(a) The converging of the stromal cells 330, which are isolated from the biological tissue 320 and moved into the culture medium 340, on the convergence parts 354a and 354b by centrifugation includes applying a centrifugal force to the stromal cells 330 by rotating the container 350 containing the stromal cells isolated from the biological tissue 320 and moved into the culture medium 340 in one direction, i.e., a normal or reverse direction, so that the stromal cells 330 may be arranged at positions symmetric to each other to be converged on the first convergence part 354a and the second convergence part 354b to which a maximum centrifugal force is applied, as illustrated in FIG. 7.

As the container 350 rotates in one direction, not only the culture medium 340 but also the biological tissue 320 and the attachment members 310 and 311 are moved to the convergence part 354a and the second convergence part 354b by a centrifugal force. In this case, the culture medium 340 passes through, together with the stromal cell 330, the first filter 370a at the entrance of the first convergence part 354a and the second filter 370b at the entrance of the second convergence part 354b and thereafter converges on the first convergence part 354a and the second convergence part 354b. However, all of the biological tissue 320 and the attachment members 310 and 311 are not allowed to pass through the first filter 370a at the entrance of the first convergence part 354a and the second filter 370b at the entrance of the second convergence part 354b and thus do not converge on both the first convergence part 354a and the second convergence part 354b. This is because the through holes of both the first and second filters 370a and 370b are adjusted to allow the culture medium 340 and the stromal cells 330 to pass therethrough but block the biological tissue 320 and the attachment members 310 and 311.

As described above, only the culture medium 340 and the stromal cells 330 converge on the first and second convergent parts 354a and 354b.

(b) The discharging of the stromal cells 330 converging on the convergence parts 354a and 354b to the outside includes discharging the culture medium 340 and the stromal cells 330 converging on the first and second convergence parts 354a and 354b to the outside as illustrated in FIG. 8.

The rotation of the container 350 is stopped when only the culture medium 340 and the stromal cells 330 converge on the first and second convergence parts 354a and 354b due to the rotation of the container 350 in one direction. Next, the culture medium 340 and the stromal cells 330 converging on the first convergence part 354a are discharged to the outside through the first stromal cell discharge part 355a on the first convergence part 354a, and the culture medium 340 and the stromal cells 330 converging on the second convergence part 354b are discharged to the outside through the second stromal cell discharge part 355b on the second convergence part 354b.

Through the above process, the stromal cells 330 isolated from the biological tissue 320 are finally collected.

By continuously performing operations (1) to (5) above, the stromal cells can be continuously isolated from the biological tissue, thereby improving isolation efficiency.

Operations (2) to (5) above may be sequentially repeatedly. Therefore, the stromal cells 330 remaining in the same attachment members 310 and 311, the biological tissue 320, or the culture medium 340 in the accommodation space 351 of the container 350 can be repeatedly collected, thereby improving the yield of the stromal cells 330.

After at least one of the biological tissue 320, the culture medium 340 or the attachment members 310 and 311 may be replaced in operations (2) to (4) above, operations (2) to (5) above may be sequentially repeated. Accordingly, the stromal cells 330 can be repeatedly collected while replacing at least one of the biological tissue 320, the culture medium 340, or the attachment members 310 and 311 remaining in the accommodation space 351 of the container 350, thereby greatly improving yield.

INDUSTRIAL APPLICABILITY

The present disclosure is applicable to a method and apparatus for isolating stromal cells from biological tissue without using an enzyme.

The invention claimed is:

1. An apparatus for isolating stromal cells from a plurality of biological tissues without using an enzyme, the apparatus comprising:
    a culture medium in which the stromal cells moving out of the plurality of biological tissues survive;
    a plurality of attachment members configured to move the stromal cells to outsides of the plurality of biological tissues by inducing spontaneous migration of the stromal cells by attaching the plurality of biological tissues to the plurality of attachment members in a culture medium; and
    a container including an accommodation space for accommodating the culture medium, the plurality of biological tissues and the plurality of attachment members, and configured to repeatedly make a normal rotation in one direction and a reverse rotation in a reverse direction to induce turbulence of the culture medium in the accommodation space,
    wherein the plurality of attachment members comprise:
    at least one first attachment member having an average specific gravity smaller than that of the culture medium, and configured to overlap at least one first biological tissue, having a smaller average specific gravity than the culture medium, of the plurality of biological tissues in a distribution area in the culture medium;
    at least one second attachment member having an average specific gravity greater than that of the culture medium, and configured to overlap at least one second biological tissue, having a greater average specific gravity than the culture medium, of the plurality of biological tissues in the distribution area;
    at least one third attachment member having the same average specific gravity as that of the culture medium, and configured to overlap at least one third biological tissue, having the same average specific gravity as the culture medium, of the plurality of biological tissues in the distribution area,
    wherein the plurality of attachment members are further configured to not only induce spontaneous migration of the stromal cells of the plurality of biological tissues to move the stromal cells to the outside of the plurality of biological tissues, when the plurality of biological tissues are attached to the plurality of attachment members in the culture medium, but also isolate the stromal cells moving to the outside of the plurality of biological tissues from the plurality of biological tissues, and
    wherein at least one of the plurality of attachment members comprises:
    a main body forming an area in which the stromal cells moving to the outside of the plurality of biological tissues by spontaneous migration are arranged; and
    a scraping portion extending outward from the main body, having a thickness less than that of the main body, and having a shape for scraping stromal cells arranged on another at least one of the plurality of attachment members.

2. The apparatus of claim 1, wherein the first attachment member comprises at least one selected from a group consisting of polypropylene, polyethylene, polyurethane, extracellular matrix (ECM), collagen, polydioxanone, polycaprolactone, poly(L-lactide) (PLLA), poly(lactic-co-glycolic acid) (PLGA), poly(lactic acid) (PLA), pterolyglutamic acid (PGA), hyaluronic acid, and silicone.

3. The apparatus of claim 1, wherein the second attachment member comprises at least one selected from a group consisting of Teflon, polycarbonate, polyethylene, phthalate, polystyrene, polyurethane, extracellular matrix (ECM), collagen, polydioxanone, polycaprolactone, poly(L-lactide) (PLLA), poly(lactic-co-glycolic acid) (PLGA), poly(lactic acid) (PLA), pterolyglutamic acid (PGA), hyaluronic acid, and silicone.

4. The apparatus of claim 1, wherein the plurality of biological tissues are finely cut to expose at least a portion of the stromal cells to the outside between collagens surrounding the stromal cells in the plurality of biological tissues, and the plurality of biological tissues are attached to the plurality of attachment members.

5. The apparatus of claim 1, wherein an angle formed by corners of a cross section of the scraping portion is an acute angle.

6. The apparatus of claim 1, wherein the container comprises an inclined portion forming the accommodation space, the inclined portion being formed to cause centrifugation when the container rotates.

7. The apparatus of claim 1, wherein the container further comprises a barrier membrane configured to block the plurality of biological tissues and allow the culture medium to pass therethrough, the barrier membrane being arranged at a position where the barrier membrane is immersed into the culture medium to prevent the plurality of biological tissues from floating on the culture medium, when the container is stopped.

8. The apparatus of claim 1, wherein the container comprises a convergence part configured to converge the stromal cells isolated from the plurality of biological tissues by a centrifugal force, the convergence part being provided at a position to which a maximum centrifugal force is applied.

9. The apparatus of claim 8, wherein the container further comprises a filter configured to allow movement of the stromal cells by a centrifugal force and block movement of the plurality of biological tissues and the plurality of attachment members, the filter being provided in a path from the container to the convergence part.

10. The apparatus of claim 8, wherein the container further comprises a stromal cell discharge part configured to discharge the stromal cells converging on the convergence part to the outside, the stromal cell discharge part being provided on the convergence part.

11. The apparatus of claim 1, wherein the container further comprises a culture medium through-tube configured to inject or discharge the culture medium, the culture medium through-tube extending from the outside to the container comprising the accommodation space which accommodates the culture medium, the plurality of biological tissues, and the plurality of attachment members.

12. The apparatus of claim 1, wherein the container further comprises a gas inlet through which a gas is injected for internal disinfection.

* * * * *